United States Patent [19]

Alfano et al.

[11] Patent Number: 5,061,075
[45] Date of Patent: Oct. 29, 1991

[54] OPTICAL METHOD AND APPARATUS FOR DIAGNOSING HUMAN SPERMATOZOA

[76] Inventors: Robert R. Alfano, 3777 Independence Ave., Bronx, N.Y. 10463; George R. Nagamatsu, 180 E., 79th St. Apt. 18E, New York, N.Y. 10021; Nobutoshi Oka, 32 Foxwood Cir., Mount Kisco, N.Y. 10549

[21] Appl. No.: 390,703

[22] Filed: Aug. 7, 1989

[51] Int. Cl.⁵ .................... G01N 21/21; G01N 21/64
[52] U.S. Cl. ............................... 356/417; 250/461.2; 356/318; 356/364
[58] Field of Search ............... 356/338, 440, 337, 342, 356/318, 327, 417, 364; 250/462.1, 458.1, 459.1, 461.2, 461.1; 436/172

[56] References Cited

U.S. PATENT DOCUMENTS

| | | | |
|---|---|---|---|
| 4,056,724 | 11/1977 | Harte | 436/172 |
| 4,115,699 | 9/1978 | Mizuta et al. | 250/461.2 |
| 4,559,309 | 12/1985 | Evenson et al. | 250/461.2 |
| 4,589,774 | 5/1986 | Dupree et al. | 356/440 |
| 4,601,578 | 7/1986 | Woolhouse et al. | 356/338 |

Primary Examiner—Vincent P. McGraw
Assistant Examiner—LaCharles P. Keesee
Attorney, Agent, or Firm—Irving M. Kriegsman; Edward M. Kriegsman

[57] ABSTRACT

The sperm count of a specimen of sperm is measured by exciting the specimen with a beam of substantially monochromatic light, then measuring the intensity of the intrinsic native fluorescence emitted or the scattered light from the specimen, and then determining the sperm count using the intensity measurements. The motitily of a specimen of sperm is determined by exciting the specimen with a beam of substantially monochromatic polarized light, then measuring the intensity of the parallel and perpendicular components of the intrinsic native fluorescene emitted or the intensity of the scattered light from the specimen at a predetermined wavelength; and then determining the motitily using the two intensity measurements with parallel and perpendicular polarizations.

15 Claims, 8 Drawing Sheets

OPTICAL METHOD AND APPARATUS FOR DIAGNOSING HUMAN SPERMATOZOA

This invention was made with Government support under Contract N00014-87-K-0431 awarded by the Department of the Navy. The Government has certain rights in this invention.

BACKGROUND OF THE INVENTION

The present invention relates generally to an optical method and apparatus for diagnosing human spermatozoa and more particularly to an optical method and apparatus for determining the sperm count and sperm motility.

It is most important to be able to determine when a male is truly subfertile. Two parameters commonly used by urologists to measure fertility are sperm count and sperm motility. Determining sperm count and motility by the well known technique of observation through a microscope is time consuming and has not been entirely satisfactory to investigators for many years. More recently, absorption spectrophotometry, dye stained fluorometry, DNA determination and flow cytometry have been used to determine sperm count while absorption spectrophotometry, time-lapse photography, cinematography, and laser light-scattering have been used to determine sperm motility. In addition, multiple exposure photography (MEP) and computer based methods of bi-level picture processing (BPP) systems have been used for quantitative evaluation of the sperm density and motility.

For more than a half a century, fluorescence, absorption, and excitation spectroscopies have been extensively used as a probe to acquire fundamental information about the various physical, chemical, and biological processes in nature. Recently, the optical methods have been extended and applied to the medical field to diagnose disease. Extrinsic fluorescent dye markers have been used but interact with the native cellular environment. The majority of the molecular systems of the cells are made of proteins, nucleic acids and lipid, with fluorescing and non-fluorescing chromophores. These systems are known to predominantly luminesce in the UV and visible spectral regions. Recently, a new technique has been developed using the "intrinsic" nature fluorophors to characterize the physiological state of the abnormal systems as compared to the corresponding normal systems. These native fluorophors display well defined spectral features that characterize the local environment and state of the cells. Their spectroscopy is sensitive to the environment of pH, redox potential, bonding sites, polarity, ion concentration and so on. Flavins are known to fluorescence in the visible spectrum region from about 510 to 530 nm. and exhibit spectral changes in different environments. Flavins are located in mitochondria.

In U.S. Pat. No. 4,290,433 to R. R. Alfano there is disclosed a technique for measuring tooth decay using fluorescence spectroscopy. Differences in the fluorescence spectra of carious and noncarious regions of teeth are clearly detected and used to determine the presence of caries. This technique has since been extended to the diagnosis of cancer and to atherosclerosis.

The following is a list of known publications pertinent to this invention:

Udenfriend, S: Fluorescenced Assay in Biology and Medicine, Vol. 1. New York: Academic Press, 1962; Udenfriend, S: Fluorescence Assay in Biology and Medicine, Vol. 2. New York; Academic Press, 1969; Pringsheim, P: fluorescence and phospherescence. New York Interscience, 1949; Fasman, G. D. Ed., Handbook of biochemistry and molecular biology, 3rd. Ed., Cleveland, Ohio: CRC Press, 1975, pp. 205-210; Chance, B., B. Schoener: Fluorometric studies of flavin compounds of the respiratory chain in Flavins and flavoprotein, E. C. Slater, Ed. Amsterdam, The Netherlands: Elsevier, 1966; Alfano, R. R. S. S. Yao: Human teeth with and without caries studies by visible fluorescent spectroscopy. J. Dent. Res. 60: 120-122, 1981; Alfano R. R., D. Tata, J. Cordero, P. Tomashefsky, F. Longo, M. A. Alfano: Laser induced fluorescence spectroscopy from native cancerous and normal tissue. IEEE J.QE. QE-20: 1507-1511, 1984; Kittrel, C., R. L. Willet, C. de Los Santose Pacheo, N. B. Ratliff, Jr., R. Kramer, E. G. Malk, M. S. Feld: Diagnosis of fibrous arterial atherosclerosis using fluorescence. app. Opt. 24: 2280-2281, 1985. Mann, T., C Lutwak-Mann, Male Reproductive function and semen, Berlin, Germany, Springer-Verlag, 1981; Badenoch, D. F., C. G. Fowler, P. R. Evans, P. A. Lowrey: DNA content of human semen-an objective measurement of sperm density. British J. Urol. 57: 230-232, 1985; Garner, D. L., Gledhill, B. L., Pinkel, D., Lake, S., Stephenson, D., Van Dilla, M. A., Jhonnon, L. A.: Qualification of the X- and Y-Chromosome-bearing spermatozoa of domestic animals by flow cytometry. Biol. Repro. 28: 312-321, 1983; and Sokoloski, J. E., L. Blasco, B. T. Storey, D. P. Wolk: Turbidimetric analysis of human sperm motitlity. Fertil. steril. 28: 1337-1341, 1977.

It is an object of this invention to provide a new and improved method and apparatus for measuring sperm count in a specimen of semen.

It is another object of this invention to provide a new and improved method and apparatus for measuring sperm motility in a specimen of semen.

SUMMARY OF THE INVENTION

According to one feature of this invention, sperm count is measured by exciting a specimen with a beam of monochromatic light, measuring the intensity of the intrinsic native fluorescence emitted from the specimen when so illuminated, and then determining the sperm count using the intensity measurement.

According to another feature of this invention, sperm motility in a specimen is determined by exciting a specimen with a beam of monochromatic polarized light, then measuring the intensity of the parallel and perpendicular component of the intrinsic native fluorescence emitted from the specimen, and then determining the motility using the two intensity measurements. In a variation of this aspect of the invention, scattered light is detected rather than fluorescence.

Various features and advantages will appear from the description to follow. In the description, reference is made to the accompanying drawing which forms a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

The present invention is directed to a method and apparatus for measuring sperm count and sperm motility using spectroscopic techniques.

More specifically, the present invention is based on the discovery that native sperm fluoresces and that the intensity of the native fluorescence and scattered light are related to the sperm count. Thus, by measuring the intensity of the native fluorescence or scattered light one can determine sperm count. The invention is also based on the discovery that if sperm is excited with polarized light the degree of the intensity of the emitted or scattered polarized light will be related to the sperm motility. More specifically, the parallel polarized component of the fluorescence will decrease and the perpendicular polarized component of the fluorescence will increase as the motility increases. Consequently, if one determines ratio of the intensity of the emitted or scattered paralled polarized light to the intensity of the emitted perpendicularly polarized light one can effectively determine the motility of the sperm. The same will apply to determine motility if polarized scattered light is detected rather than polarized emitted light.

Figure 1:
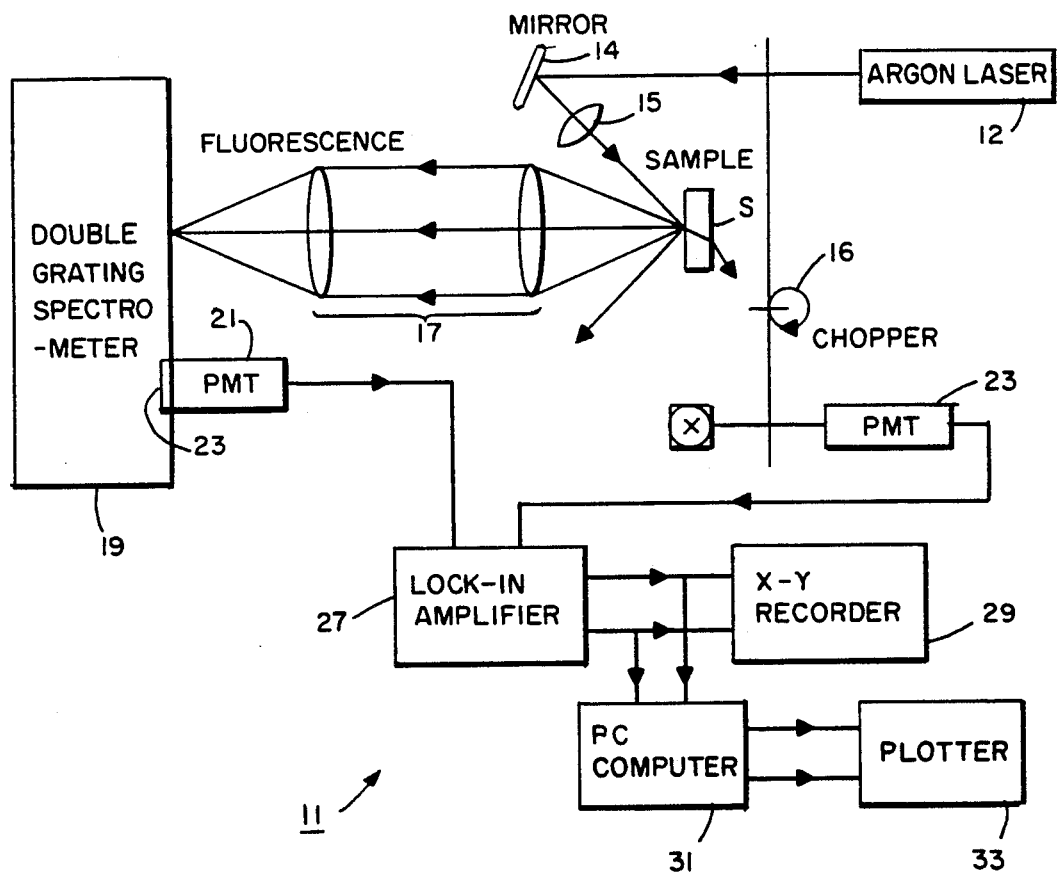
FIG. 1 is a schematic of an experimental set up used for measuring the fluorescence spectra according to this invention.

Referring now to the drawings, an experimental arrangement 11 used to measure the fluorescence spectra from semen, seminal plasma and spermatozoa is shown in FIG. 1. Light from an Argon-ion laser 12 (Lexel) operated at 488 nm was deflected off a mirror 14 and focused by a lens 15 on the front surface of a sample which was located in a curvette. The laser power was set to 15 mw at sample site, for sensitivity of 0.5 to 1 mv for lock-in detection system. The light beam laser was chopped by a chopper 16 at 200 Hz. The fluorescence from the front surface of the specimen was collected and focused by a lens system 17 onto the entrance slit of a double ½ m grating scanning spectrometer 19 (SPEX Industries Inc., Metuchen, N.J.) blazed at 500 nm. A Photomultiplier tube (PMT), RCA 7265 (S-20) located at the exit slit 23 of the spectrometer measured the intensity at different wavelengths. The spectral resolution was about 2 nm. The output of PMT 21 and a reference signal from a PMT 23 was connected to a lock-in-amplifier 27 (EG&G Princeton Applied Research Corp., Princeton, N.J.) and an X-Y recorder 29 combination to display each spectrum. The output of lock-in amplifier 27 was also connected to a computer 31 coupled to a plotter 33. The fluorescence spectrum was calibrated with standard Rhodamine 6G solution.

To obtain the test samples, specimens of semen were collected from a fertile male by masturbation after 5 days of sexual abstinence. Semen specimens were kept for 30 minutes at room temperature. After liquefaction, the following analysis were performed: volume and pH of semen; sperm density and motility rate.

Figure 2:
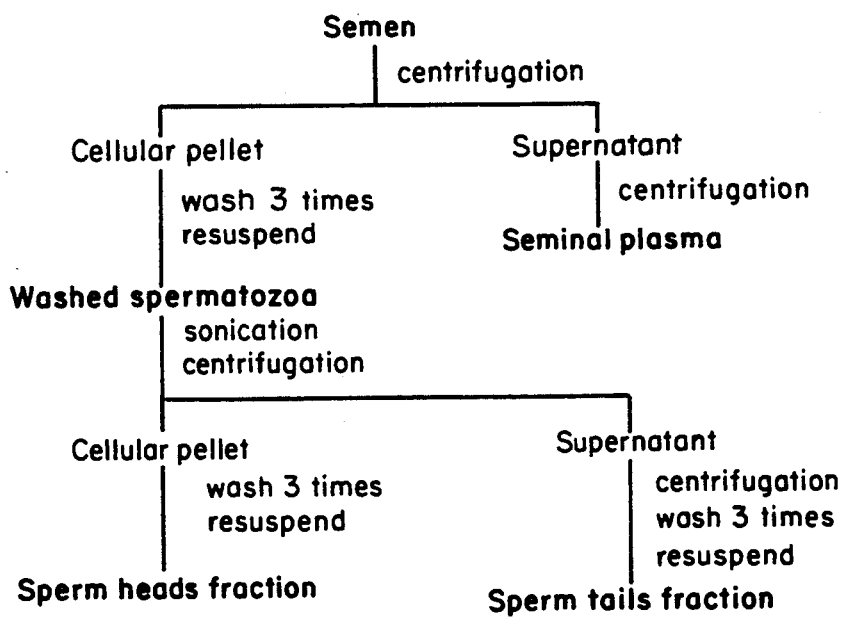
FIG. 2 is a chart showing the procedure used in connection with the experimental setup in FIG. 1 for separation of spermatozoa.
Figure 3A:
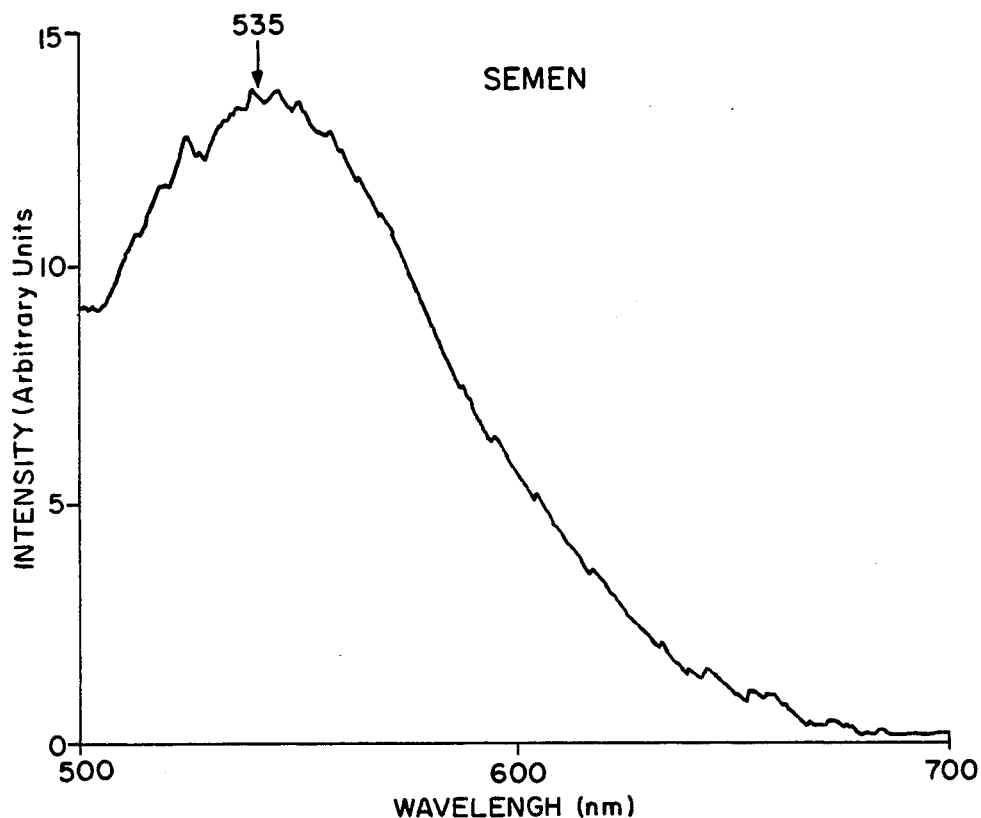
FIGS. 3(a) through 3(f) are curves of fluorescence spectra excited at 488 nm for semen, seminal plasma, washed spermatozoa fraction, sperm head fraction, sperm tail fraction, and PBS, respectively using the experimental setup of FIG. 1.
Figure 3B:
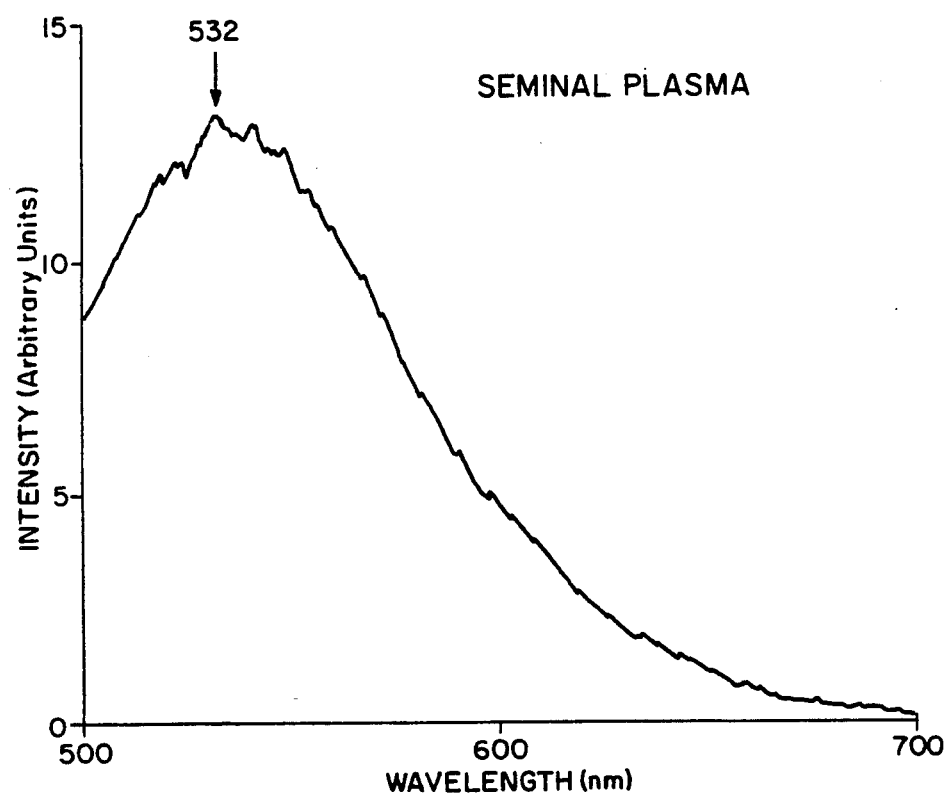
Figure 3C:
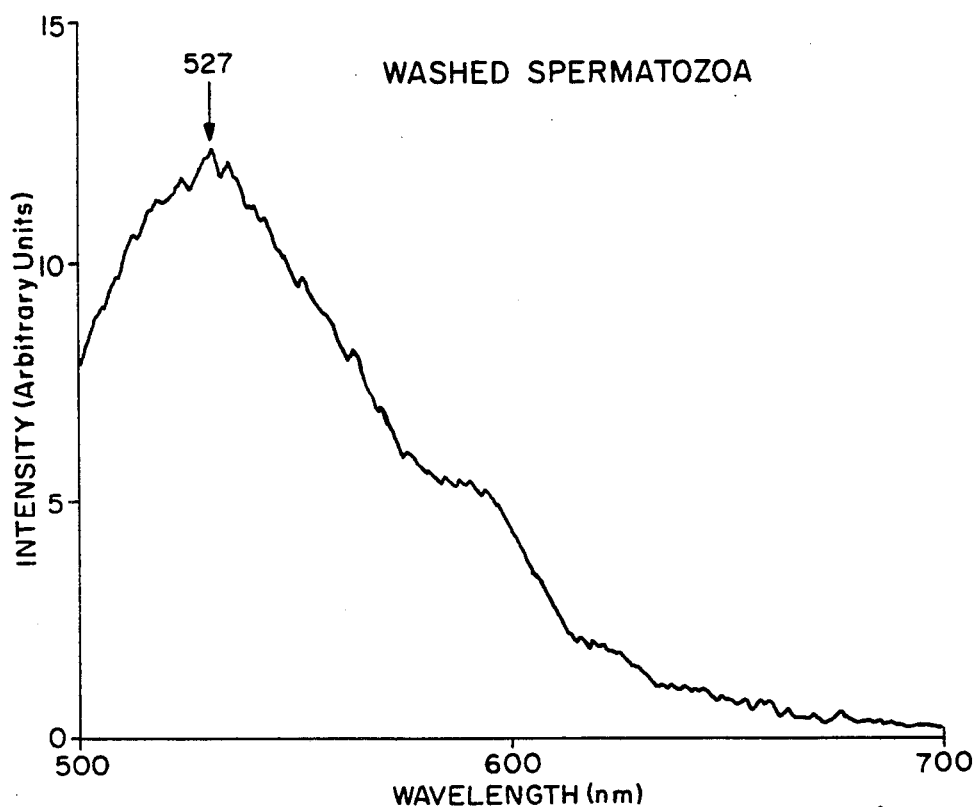
Figure 3D:
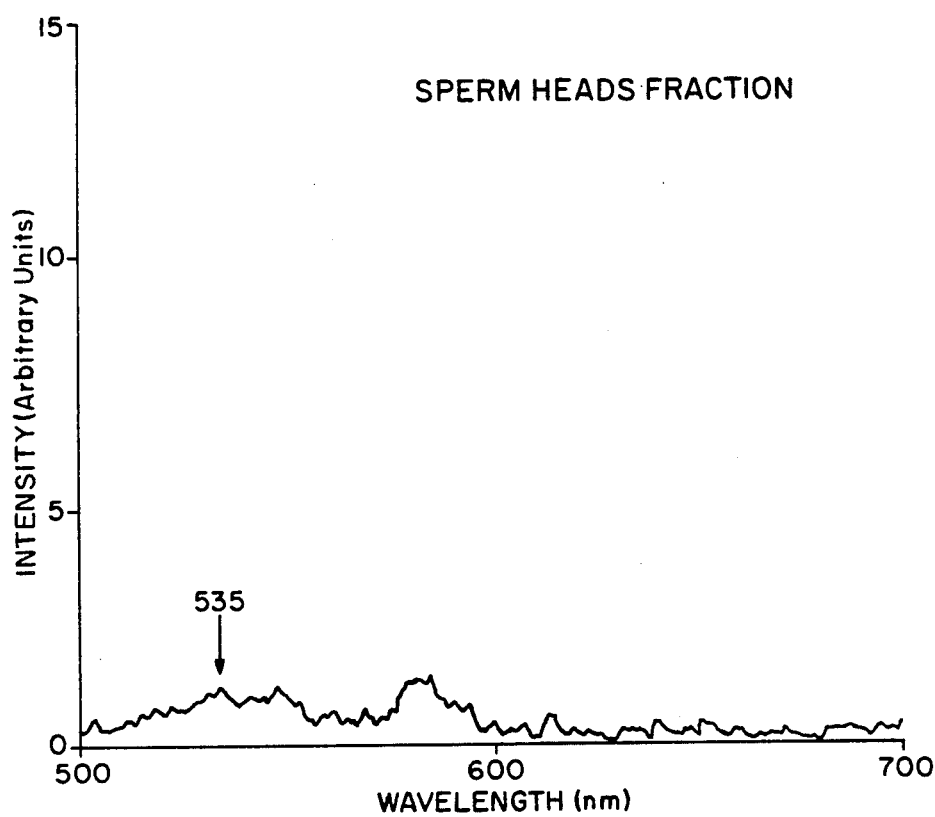
Figure 3E:
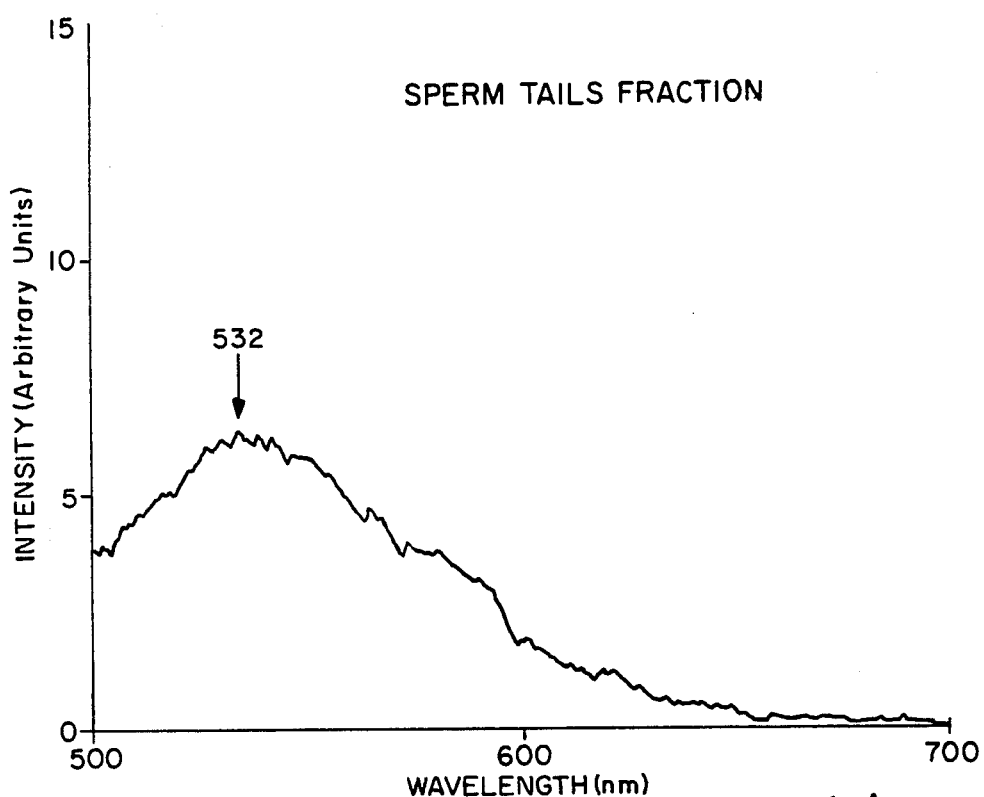
Figure 3F:
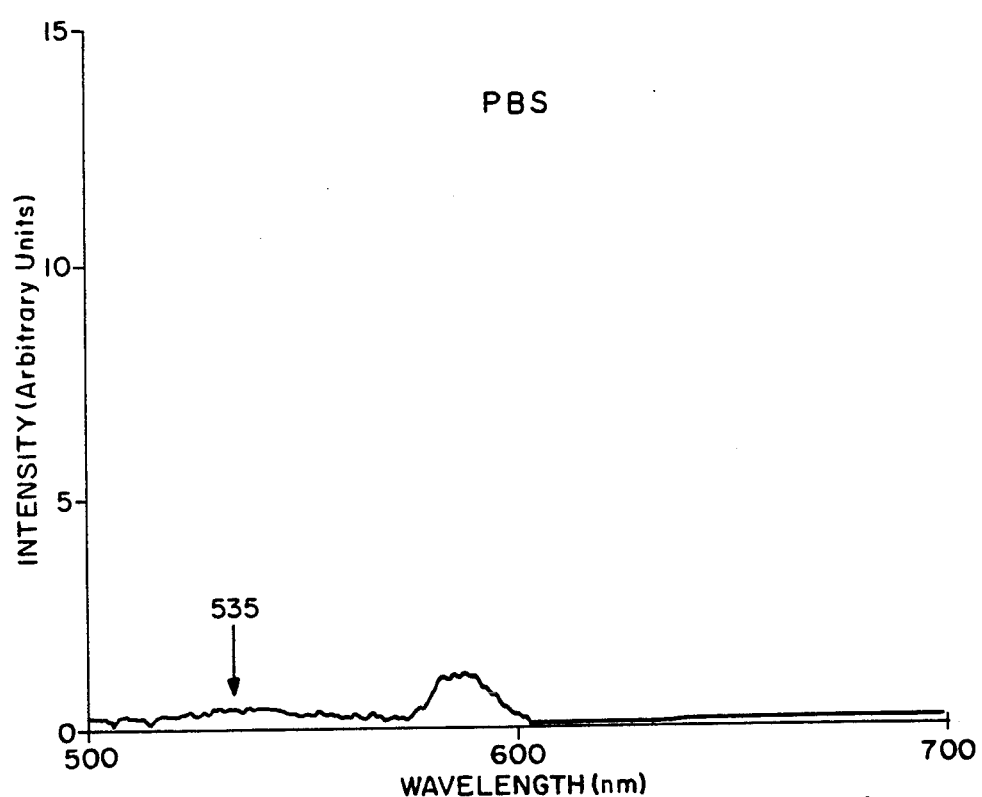

The preparation procedure for the sperm fractions is shown in FIG. 2. Semen of 500 l were micropipeted and centrifuged at 3,000 rpm for 10 min. Supernatant was removed by micropipet, washed three times witih phosphate buffered saline (PBS), pH 7.4 and resuspended in 0.5 mL PBS for washed spermatozoa fraction. Sperm suspension was sonicated with Sonifier (Branson Sonic Power Co. Danbury, Conn.) at force 7 for 3 min on ice and centrifuged at 3,000 rpm for 10 min. Cellular pellet was washed three times and resuspended in 0.5 ml PBS for sperm tails fraction. Each fraction was stained by eosin Y (Sigma, St. Louis, Mo.) solution and examined by microscopy. All samples were examined for sperm count using a Makler chamber and for pH using pH170 pH meter (Beckman, Fullerton, Calif.). All sample components used for fluorescence measurements were native (No dyes were added).

To examine the relation between the intensity of fluorescence spectra and sperm count, washed spermatoza were diluted serially with PBS.

Typical fluorescence spectra from semen, seminal plasma, washed spermatozoa, sperm heads, sperm tails, and PBS photoexcited at 488 nm are shown in FIGS. 3, (a) to (f), respectively. One notices the spectra profile's shape are different for semen, seminal plasma, washed spermatozoa, sperm heads, sperm tails and PBS. The principal spectral peaks are located at 535 nm for semen; at 532 nm for seminal plasma; at 527 nm, for washed spermatozoa; at 535 nm for sperm heads; at 532 nm for sperm tails; and at 535 nm for PBS. The relative intensity for each components are as follows: semen, 185; seminal plasma, 202; washed spermatozoa, 13.8; sperm heads, 1; and sperm tails, 6.3. The fluorescence spectra from PBS was very weak. In washed spermatozoa, sperm head, and sperm tails, there are one main peak with a small subsidiary peak from Raman scatter from the PBS solution. As can be appreciated, the Raman line can be used as an internal calibration to determine sperm count. Semen and seminal plasma spectra showed a monotonic decrease with no clear subsidiary maximum. This experiment was repeated for three different sample runs with similar results.

Figure 4:
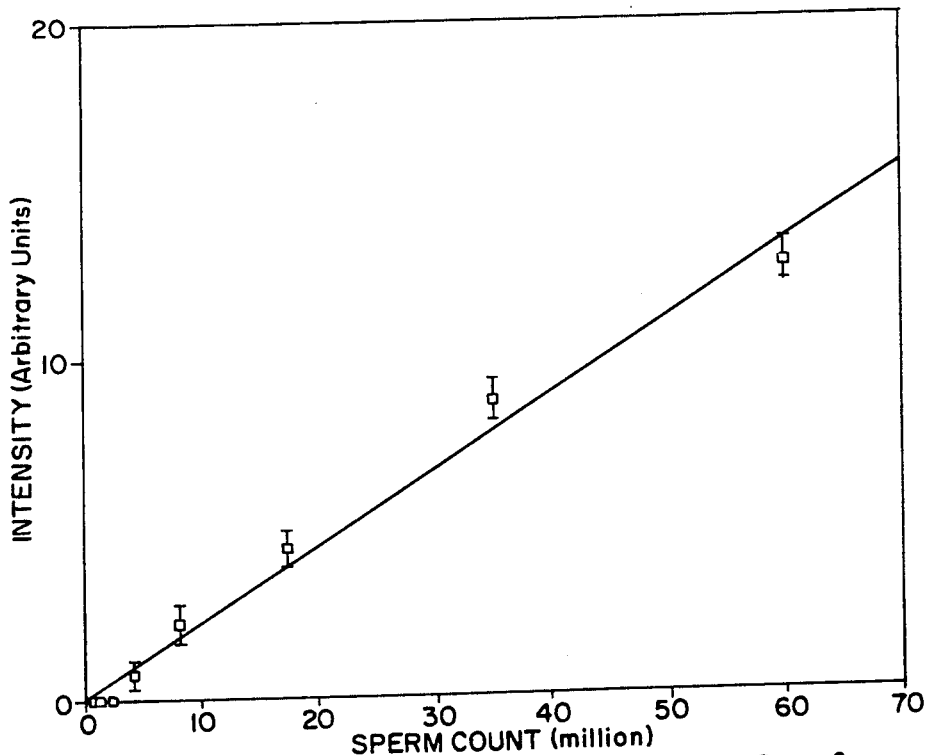
FIG. 4 is a curve showing the relationship between the sperm count and intensity of the fluorescence spectra from washed spermatozoa.

The relationship between the intensity of spectra and sperm count, using a Makler chamber to actually determine the sperm count for each specimen, is plotted in FIG. 4. There was excellent correlation between the intensity of spectra and sperm count ($r+0.99$, $p<0.01$).

At present, the lowest detected sperm count was about $1 \times 10^6$ sperms.

Figure 5:
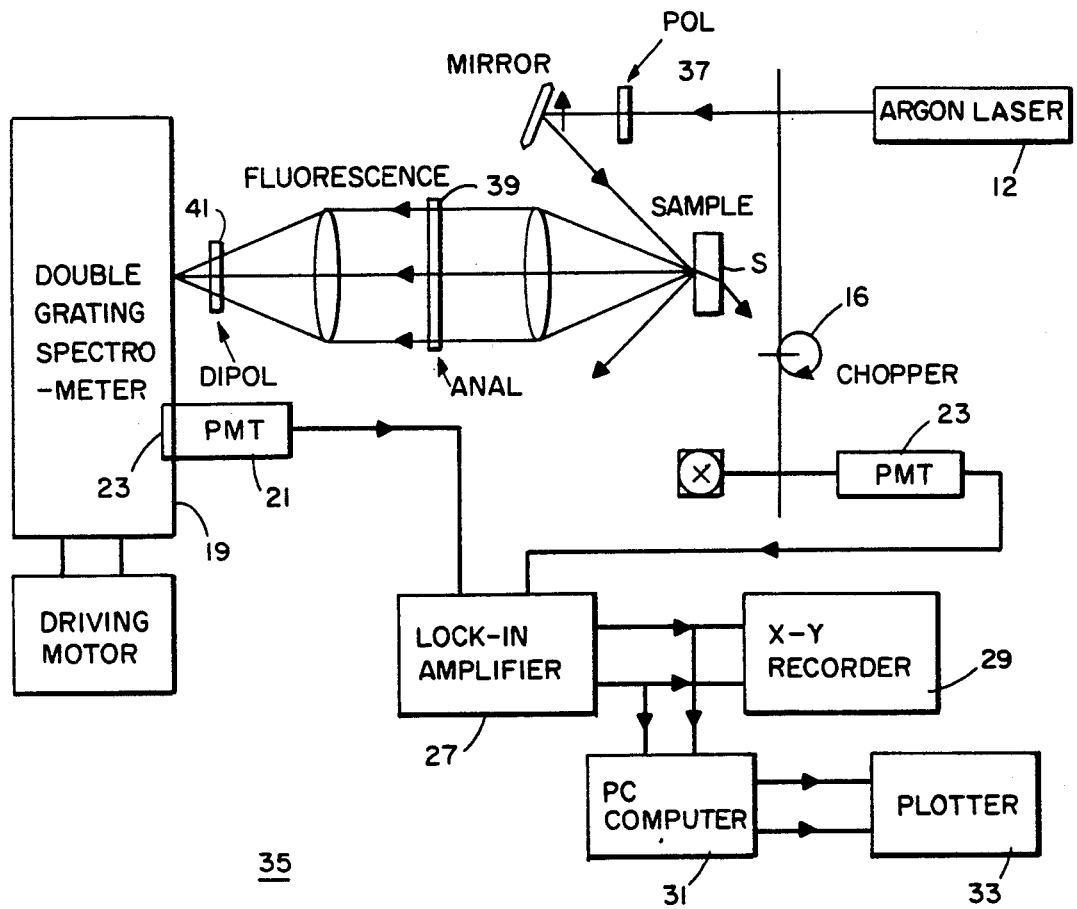
FIG. 5 is a schematic of an experimental set up for measuring the fluorescence polarization.

An experimental apparatus 35 for measuring sperm motility is shown in FIG. 5. Apparatus 35 differs from apparatus 11 in that it also includes a polarizer 37 for polarizing the output beam from laser 13, an analyzer 39 which can be rotated so as to pass either the parallel polarized component of the light emitted from the specimen or the perpendicularly polarized component of the light emitted from the sample and a depolarizer 41 to depolarize the light entering spectrometer 19.

Using the apparatus in FIG. 5, the intensity of the parallel or perpendicular components of the sample's luminescence as functions of wavelengths were each measured on separate scans. The degree of polarization was computed from the equation: $P=(I_\perp-I_\parallel)/(I_\perp+I_\parallel)$ where $I_\parallel$ and $I_\perp$ are the intensity of the parallel and perpendicular components of the polarized light, respectively.

Figure 6:
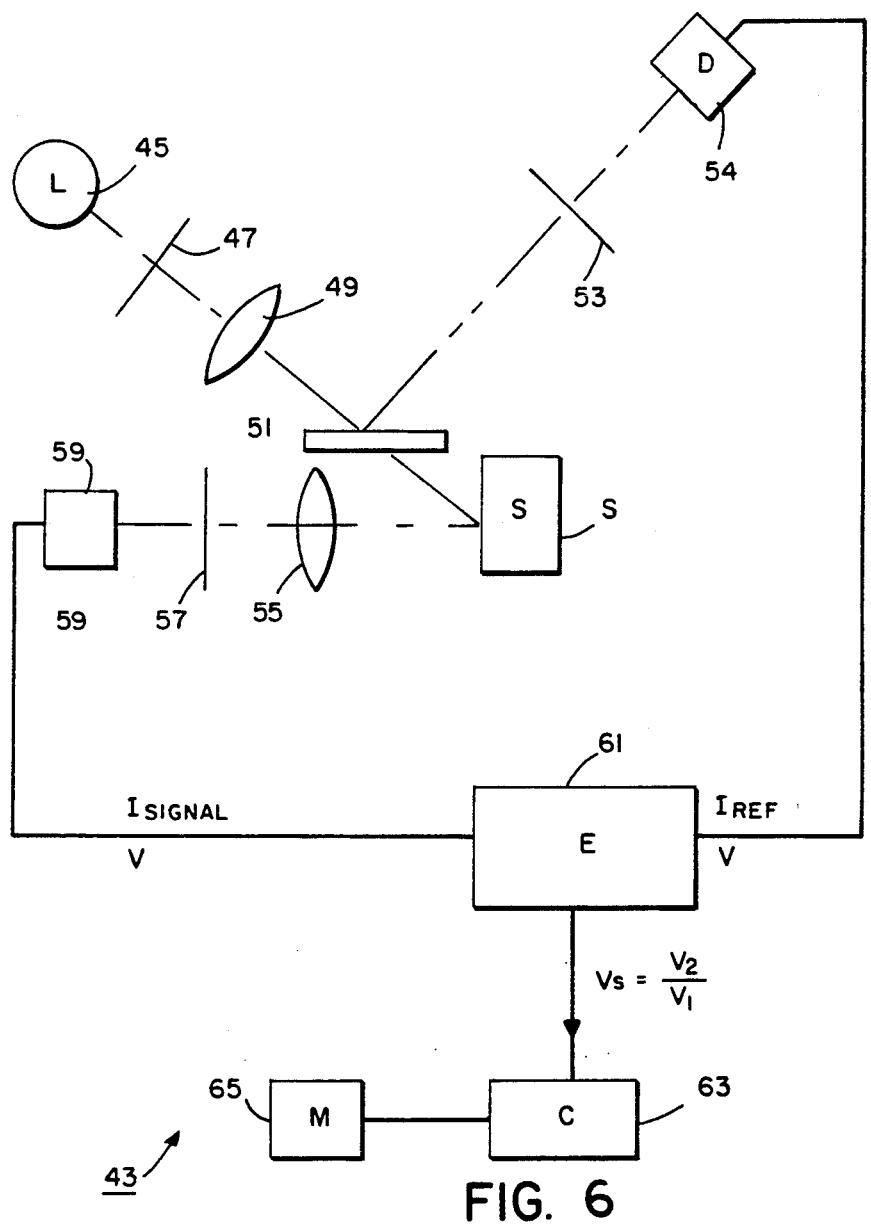
FIG. 6 is a schematic of an apparatus for measuring sperm count according to this invention.

Referring now to FIG. 6, there is shown an embodiment of an apparatus 43 for measuring the sperm count in a sample S of sperm. The sample S is prepared initially by taking a specimen of semen, centrifuging the specimen to remove the supernatant, washing the remaining sperm three times and then resuspending the washed sperm in PBS.

A beam of light from a source 45 of white light such as a tungsten-halogen filament lamp is passed through a narrow band filter 47 which has a bandwidth of preferably less than 10 nm and designed to pass light at $\lambda_1$, which is preferably less than 500 nm and then after passing through a focusing lens 49 strikes a beamsplitter 51. The beam passed through beamsplitter 51 is brought to focus by lens 49 on sample S while the reflected beam is passed through another filter 53 identical to 47 and then brought to focus by lens 49 onto a photodetector 54. At least some of the fluorescence emitted from sample S is collected by a lens 55 and then passed through a narrow band filter 57 designed to pass the fluorescence radiation at a wavelength $\lambda_2$. $\lambda_1$ may be, for example, 488 nm and $\lambda_2$ 532 nm. The light passed through filter 57 is brought to focus by lens 55 at a photodetector 59. The output signals $V_1$ and $V_2$ of the two photodetectors 54 and 59, respectively, is fed into electronics 61 which outputs a voltage signal $V_s$ corresponding to the ratio of the output signal from photodetector 59 and the output signal from photodetector 54, i.e.

$$\frac{V_2}{V_1},$$

the signal corresponding to the ratio of the intensity of the light striking photomultiplier tube 59 ($I_s$) to the intensity of the light striking photodetector 54 ($I_{REF}$). Electronics 61 may comprise any conventional type of dividing circuit. Photodetectors 54 and 59 may, for example, be photomultiplier tubes. Instead of a white light type of light source a laser, such as an argon laser which outputs light at 475 and 488 nm may be employed and, if desired, filter 47 eliminated. Instead of a dividing circuit, the electronics may comprise a difference or multiplying circuit.

Figure 7:
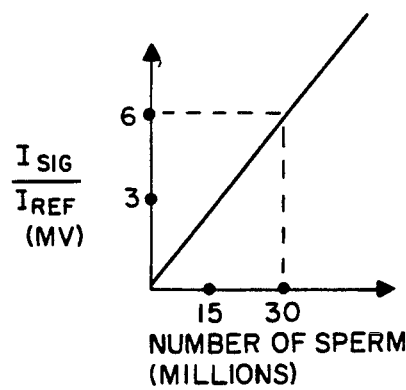
FIG. 7 is a graph useful with the apparatus of FIG. 6.

The output voltage $V_s$ is fed into a computer 63 which performs a table look-up and other processing as needed or desired and displays the results on a monitor 65. A graph showing the table look-up performed by a computer 63 is illustrated in FIG. 7. For example, a voltage signal $V_s$ of 6 millivolts will result in a table lookup of 30 million sperms.

Figure 8:
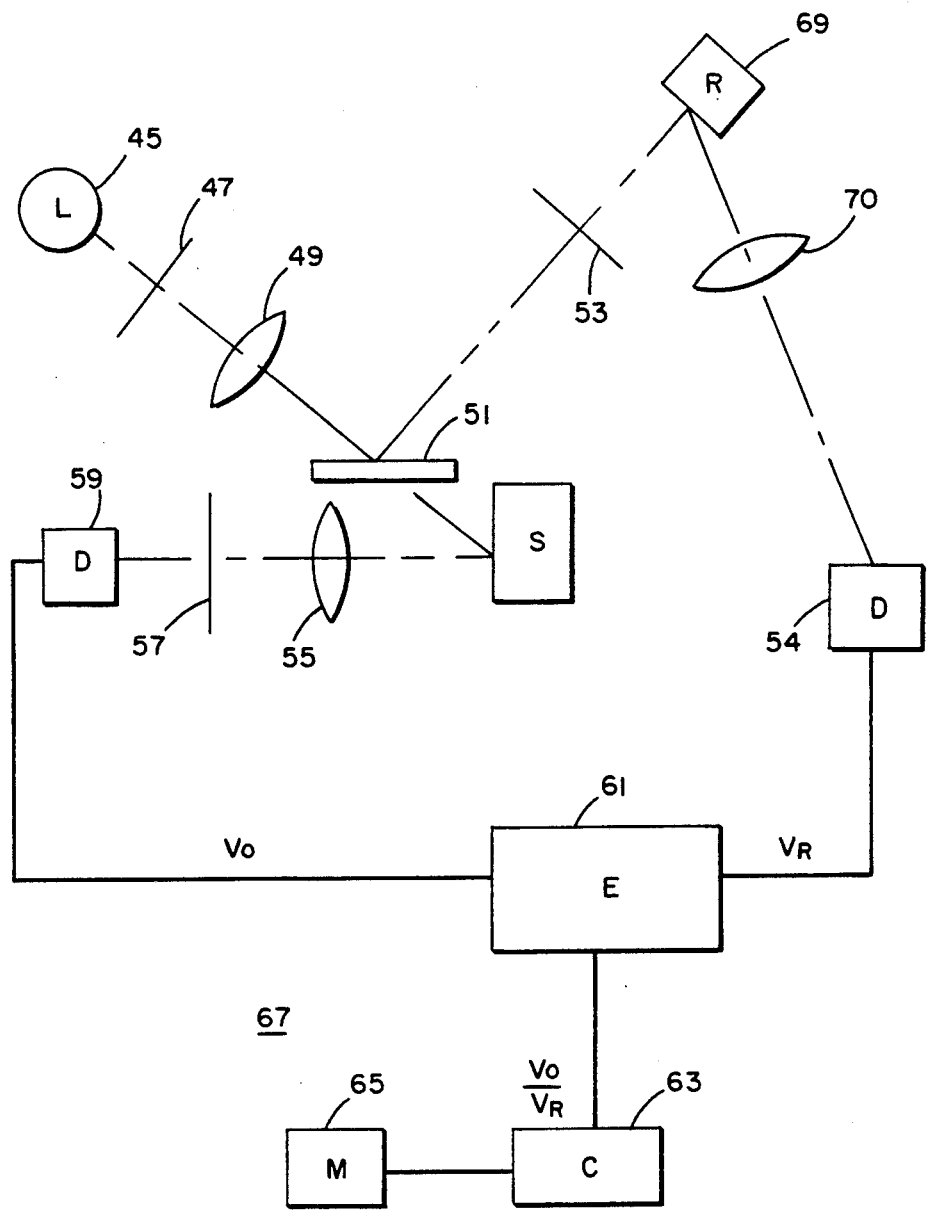
FIG. 8 is schematic of another embodiment of an apparatus for measuring sperm count according to this invention.
Figure 9:
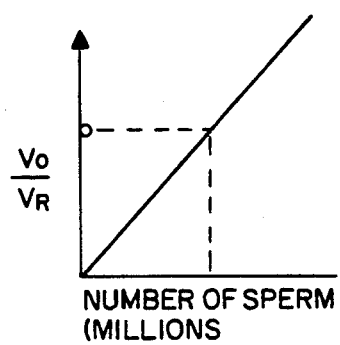
FIG. 9 is a graph useful with the apparatus of FIG. 8.

Referring now to FIG. 8 there is shown a schematic of another embodiment of an apparatus for measuring sperm count according to this invention, the apparatus being identified by reference numeral 67. Apparatus 67 differs from apparatus 54 in that the light reflected off of beamsplitter 51 does not impinge a photodetector 53 but rather strikes a reference unit 69, such as a dye in a plastic holder. The fluorescent radiation emitted from reference unit 69 is collected and brought to focus by a lens 70 on photodetector 53. The voltage signal outputted from photodetector 54 is, accordingly, related to the intensity of fluorescent radiation emitted from reference unit 69 rather than simply the intensity of the light reflected by beamsplitter 51. A graph corresponding to the look-up table in computer 63 is shown in FIG. 9.

Figure 10:
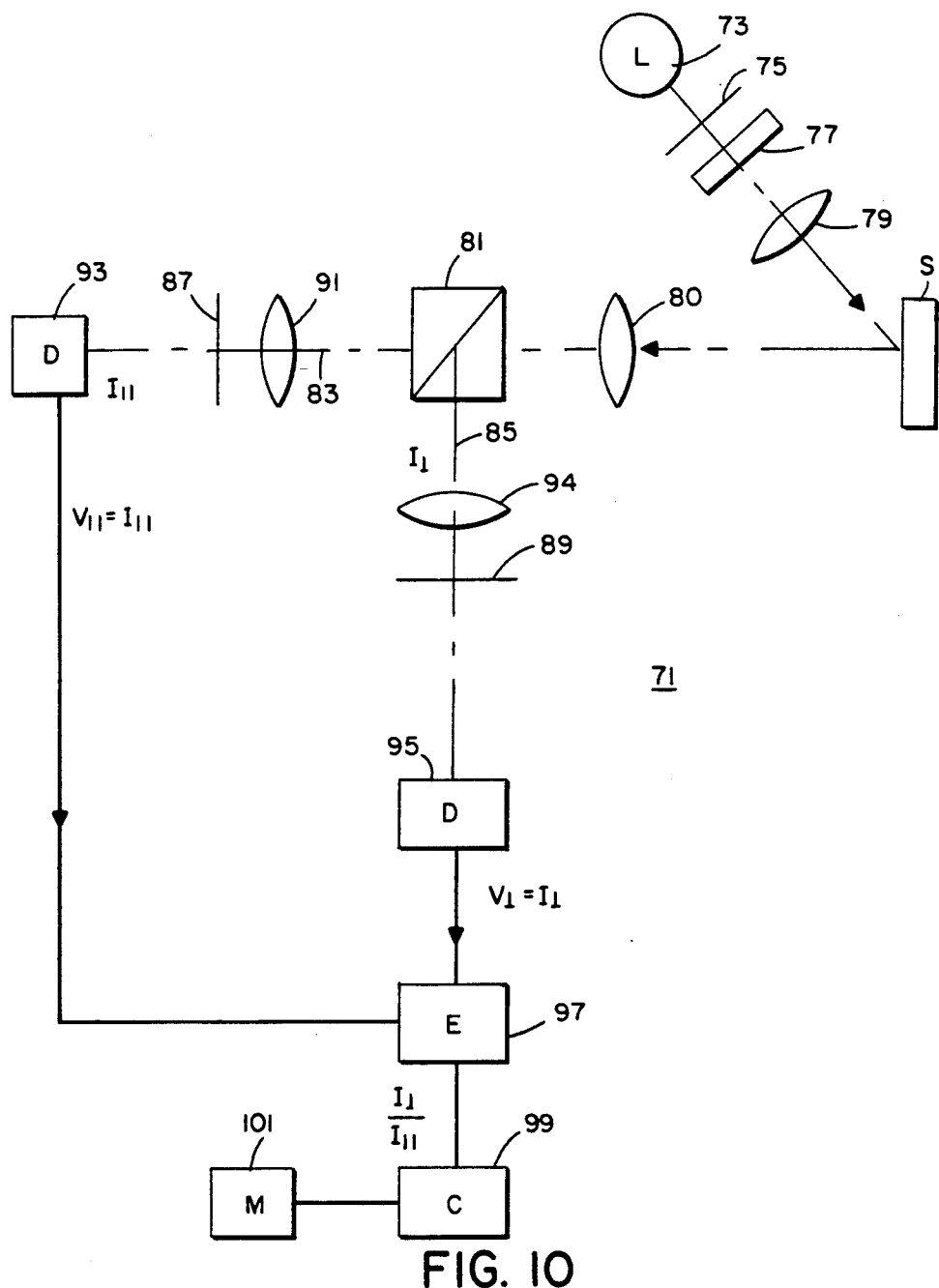
FIG. 10 is a schematic of an apparatus for measuring motility according to this invention.

Referring now to FIG. 10 there is shown an apparatus for measuring sperm motility according to this invention, the apparatus being identified reference numeral 71.

Light from a source 73 such as a tungsten-halogen filament lamp or a laser, is passed through a narrow band filter 75 designed too pass light at a desired wavelength, then through a polarizer 77 and then brought to focus by lens 79 on the sample S. If source 73 is a laser whose output is sufficiently polarized then polarizer 77 may be eliminated.

The light emitted from the sample S includes two components, one polarized parallel to the polarized light in the incident beam and the other polarized perpendicular to the parallel component. The light is collected and collimated by a lens 80 and strikes a Nicol prism 81.

Figure 11:
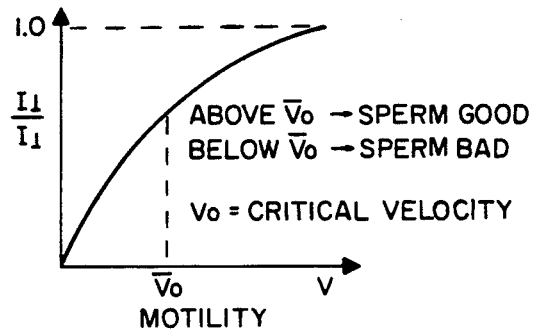
FIG. 11 is a graph useful with the apparatus of FIG. 10.

A Nicol prism 81 splits the emitted beam into two beams, one identified by reference numeral 83 and containing only the parallel component and the other identified by reference numeral 85 and containing only the perpendicular component. Light traveling along path 83 is passed through a narrow band filter 87 designed to pass light at a predetermined frequency and light traveling along path 85 is passed through a similar narrow band filter 89. A lens 91 focuses the light passed by filter 87 on a detector 93 and a lens 94 focuses the light passed by filter 89 on a detector 95. The output voltage signal of detectors 93 ($V_\parallel$) which is related to the intensity of the light impinging thereon ($I_\parallel$) and the output voltage signal ($V_\perp$) of detector 95 which is related to the intensity of the light impinging thereon ($I_\perp$) is fed into electronics 97 which takes the ratio of the two signals i.e.

$$\frac{I_\perp}{I_\parallel}$$

and feeds the output into computer 99 where a table look-up and other processing are performed. The results are then displayed on monitor 101. A chart illustrating the table look-up performed in computer 99 is shown in FIG. 11.

Instead of taking the ratio of the two voltage signals i.e. the electronics may comprise circuitry for taking the ratio of the difference and sum of the two voltage signals may be taken i.e.

$$\frac{I_\perp - I_\parallel}{I_\perp + I_\parallel}$$

or the product of the two signals $I_\perp \times I_\parallel$. Also, spectrometers may be employed instead of filters 87 and 89. Also instead of measuring the intensity of the parallel and perpendicularly polarized components of the emitted light, the intensity of the parallel and perpendicularly polarized components of the scattered light can be measured. This can be achieved by simply changing filters 87 and 89 so as to pass scattered rather than emitted light.

The embodiments of the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of measuring the sperm count in a specimen of sperm comprising:
   a. exciting the specimen with a beam of monochromatic light,
   b. measuring the intensity of the intrinsic native fluorescence emitted from the specimen, and then
   c. determining the sperm count using the intensity measurement.

2. The method of claim 1 and wherein determining the sperm count using the intensity measurement includes determining the ratio of the intensity measurement so measured and the intensity of a reference signal and then using that ratio to determine the sperm count.

3. The method of claim 2 and wherein the exciting light is at about 488 nm and the fluorescence measured is at about 535 nm.

4. The method of claim 2 and wherein determining the sperm count comprises comparing the ratio with a standard.

5. Apparatus for measuring the sperm count of a specimen of sperm comprising:
   a. means for exciting the specimen with a beam of monochromatic light,
   b. means for measuring the intensity of the intrinsic native fluorescence emitted from the specimen, and
   c. means for determining the sperm count using the intensity measurement.

6. The apparatus of claim 5 and wherein the means for exciting the specimen comprises either a lamp with a filter or a laser.

7. The apparatus of claim 6 and wherein the laser is either a solid, a gas or a semiconductor.

8. The apparatus of claim 6 and wherein the laser is either an argon laser, a He-Ne laser a He-Cd laser a dye laser or a semiconductor laser.

9. The apparatus of claim 5 and wherein the determining means includes a computer.

10. The apparatus of claim 5 and wherein the means for determining sperm count using the intensity measurement includes means for generating a reference signal and means for producing an output signal related to the intrinsic native fluorescence emitted from the sample and the reference signal.

11. A method of determining the motility of a specimen of sperm comprising:
    a. exciting the specimen with a beam of monochromatic polarized light,
    b. measuring the intensity of the parallel and perpendicular components of the intrinsic native fluorescence emitted from the specimen, at a predetermined wavelength, and then
    c. determining the motility using the two intensity measurements.

12. Apparatus for determining the motility of a specimen of sperm comprising:
    a. means exciting the specimen with a beam of monochromatic polarized light,
    b. means measuring the intensity of the parallel and perpendicular components of the intrinsic native fluorescence emitted from the specimen at predetermined wavelength, and
    c. means determining the motility using the two intensity measurements.

13. The apparatus of claim 12 and wherein the measuring means includes a Nicol prism for splitting the intrinsic native fluorescence emitted from the specimen into two beams, one having only polarized light parallel to the incident beam and the other having only polarized light perpendicular to the incident beam.

14. A method of determining the sperm count in a specimen, the sperm being obtained from a sample of semen which has been centrifuged to remove the plasma, washed and then resuspended, the method comprising:
    a. exciting the specimen with a beam of monochromatic light,
    b. measuring the intensity of the intrinsic native fluorescence emitted from the specimen, and then
    c. determining the sperm count using the intensity measurement.

15. A method of determining the motility of a specimen of sperm comprising:
    a. exciting the specimen with a beam of polarized light,
    b. measuring the intensity of the parallel and perpendicular components of the light scattered from the specimen, and then
    c. determining the motility using the two intensity measurements.

* * * * *